United States Patent
Polaschegg

(10) Patent No.: US 6,803,363 B2
(45) Date of Patent: *Oct. 12, 2004

(54) PERITONEAL DIALYSIS SOLUTION WITH TAUROLIDINE

(75) Inventor: Hans-Dietrich Polaschegg, Koestenberg (AT)

(73) Assignee: ND Partners, LLC, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/160,529

(22) Filed: May 31, 2002

(65) Prior Publication Data

US 2003/0225066 A1 Dec. 4, 2003

(51) Int. Cl.⁷ .......................... A61K 31/54; A61M 1/00
(52) U.S. Cl. ...................................... 514/222.5; 604/29
(58) Field of Search .......................... 514/222.5; 604/29

(56) References Cited

U.S. PATENT DOCUMENTS

| | | | | |
|---|---|---|---|---|
| 4,980,374 A | * | 12/1990 | Steudle et al. | 514/557 |
| 6,258,797 B1 | * | 7/2001 | Lehner | 514/56 |
| 6,423,706 B2 | * | 7/2002 | Sodemann | 514/222.5 |

* cited by examiner

*Primary Examiner*—Frederick Krass
(74) *Attorney, Agent, or Firm*—Burns & Levinson, LLP; Frederick C. Williams; Yan Lan

(57) ABSTRACT

The present invention contemplates the addition of 0.5% to 4% taurolidine into solutions used peritoneal dialysis. The taurolidine is intended to prevent or reduce the incidence of infection within the abdomen and/or in the vicinity of an implanted dialysis port. The invention also includes methods using solutions of taurolidine in the flushing and locking of catheters and fluid lines used in peritoneal dialysis.

6 Claims, 1 Drawing Sheet

PERITONEAL DIALYSIS SOLUTION WITH TAUROLIDINE

FIELD OF THE INVENTION

The present invention relates generally to solutions used in dialysis, i.e., in purification of blood by artificial means. More specifically, the present invention relates to the water-based chemical solutions used in the process of continuous ambulatory peritoneal dialysis and it further relates to anti-microbial compounds for use therein.

BACKGROUND OF THE INVENTION

Dialysis is a medical therapy by which to achieve the blood-purifying function normally performed by the kidneys. Dialysis is most generally used in cases of chronic or acute renal insufficiency or failure associated with kidney disease or injury or during kidney operations or transplantations.

During dialysis, a patient's blood, overloaded with catabolites (i.e., blood-borne metabolic waste), is brought into close contact with an artificial dialysis solution. (The terms "dialysis solution," "dialysis fluid," and "dialysate" are used interchangeably herein and have the same meaning.) The blood and the dialysis solution are separated from one another by a semipermeable membrane that can be either artificial or natural. The dialysis solution is formulated to be isotonic and in such a way that blood-borne catabolites cross the membrane from the blood to the dialysis solution by diffusion, thereby reducing the blood concentration of catabolites. The other critical function of dialysis is the removal of excess water from the body.

The efficiency of dialysis is directly related to a number of factors including at least volume of dialysis fluid, number of changes of dialysis solution and length of time between changes (or flow rate in a continuous system), surface area of membrane, pore size of the membrane, rates of diffusion of the toxins, and patient variables.

Hemodialysis is a specific type of dialysis in which the patient's blood is withdrawn temporarily from the patient's body and shunted through a machine containing the membrane and dialysis solution as well as pumps and temperature controls. Provision is made for blood to be drawn from the patient's body and thence circulated through the machine, wherein it is exposed to the membrane surface. The catabolites migrate out across the membrane and water is removed by mechanical filtration. The treated blood is then returned to the patient's body. Water is generally removed by hydraulic pressure across the membrane.

An alternative to hemodialysis is peritoneal dialysis (PD), which takes advantage of the living tissue membrane that lines the patient's peritoneum, the peritoneum being the portion of the abdominal cavity located below the diaphragm and which contains the viscera. The principal difference between peritoneal dialysis and hemodialysis is substitution of the natural semipermeable capillary bed membranes that are abundant within the peritoneal cavity for the artificially provided semipermeable membranes of the hemodialysis machine.

In PD, the dialysis solution is introduced into the patient's peritoneal cavity by way of an abdominal port or catheter. The dialysis solution is left inside the patient's peritoneum for a period ranging from a few hours to overnight and then removed. During PD, that portion of the patient's blood flowing most adjacent toe peritoneal membrane undergoes the blood-cleansing dialysis process. That is, the catabolites migrate across the patient's peritoneal membrane from the blood to the dialysis solution. By flooding the interperitoneal extravascular space with isotonic dialysis solution, exchange of toxins from the blood occurs and dialysis is accomplished.

The concept of continuous ambulatory PD was introduced in the U.S. by Popovich and Moncrief in 1976. These authors revealed a method for continuous ambulatory peritoneal dialysis (CAPD), whereby the patient carries a bag made of a soft material, such as polyvinyl chloride, which contains the dialysis solution. The container of dialysis solution is connected through a tube from the soft bag into the peritoneal cavity of the patient.

In current day PD practice, a port or a catheter is placed within a patient's abdomen so that it traverses the body's outer surface. The port or catheter allows fresh dialysis solution to be introduced into the patient's peritoneal cavity and drained from the peritoneal cavity once the solution becomes ineffective or spent, i.e., when the concentration of catabolites removed from the patient's blood reaches a level in the dialysis solution that renders the solution inefficient at removing additional metabolites from the patient's blood.

Typically, PD systems are configured such that there is a drain line and a fresh dialysis line attached to the end of the catheter protruding from the patient. Further, the connections between the fresh dialysis line and the catheter, the drain line and the catheter, and the fresh dialysis line and the drain line are all capable of being opened and closed as necessary. This allows for various techniques for filling and draining the peritoneal cavity with a dialysis solution.

PD has a distinct advantage over hemodialysis in that it allows the patient to receive treatment while performing normal daily activities without the sense of being incapacitated. Ambulatory continuous peritoneal dialysis normally takes place with approximately 4 exchanges per 24 hours.

With respect to water removal, in PD it is impossible to create a pressure gradient across the peritoneal membrane for the removal of water from the patient's blood. Therefore, in PD, osmotic ultrafiltration is the mechanism whereby water is extracted from the blood to the dialysate. Water removal is achieved by providing a dialysis fluid with approximately normal blood electrolyte concentration and with an additional substance of preferably low diffusivity. Net water removal is achieved because water diffuses to the peritoneal cavity faster than the osmotic substance diffuses from the peritoneal cavity to the blood. The substance most commonly used is glucose, which diffuses into blood and achieves equilibrium within a few hours. The additional glucose load is normally acceptable because glucose is rapidly metabolized.

Osmotic ultrafiltration during PD is achieved by adding a large amount of, e.g., glucose to the dialysis solution as a way to maintain an initial high concentration of solute on the side of the membrane to which water is to flow from the blood to the dialysate. Glucose also prevents back flow of water from the dialysis solution into the patient's blood. Alternative osmotic agents are amino acids, glycerol, or poorly absorbable carbohydrate polymers still under investigation.

A major likely complication of PD is peritonitis, i.e., infection of or within the peritoneal lining or peritoneal cavity respectively. The major route for infection is the catheter connection. For this reason many developments have been devoted to avoid contamination of the inner lumen of the fluid pathway during the connection process.

UV-light and heat has been used to reduce bacterial contamination after connection. Conventional connectors have been replaced by special ones reducing the likelihood of contamination by skin contact. Also, methods have been developed reducing the likelihood of contamination, e.g., flushing fresh dialysate to drain initially before spent dialysate is removed.

Implanted ports and catheters through which the dialysis solution is introduced to and retrieved from the peritoneum also contribute to the incidence of peritonitis. Such port and catheters are disposed neither completely within the sterile realm of the body nor completely external to the body; that is, the ports and/or catheters used in dialysis traverse the body's outer surface, thereby in effect exposing the sterile in-body realm to the pathogens of the outside world.

Additionally, the substances contained within dialysis solutions, especially glucose, dextrose, amino acids, and glycerol as mentioned above are conducive to the growth of bacteria. Therefore, even if the dialysis solution is sterile, the constituents of the solution can serve as an ideal culture medium for bacterial growth.

Moreover, the process of implantation of a peritoneal dialysis port or catheter provokes the body's tissues most adjacent to the implanted device to form a tissue pocket or capsule around the implanted device. The capsule is the body's way of isolating the foreign object from the body's larger system. Typically the walls of such a tissue pocket or capsule have a thickness of a millimeter, more or less. Bacterial infection within the tissue pocket or capsule can take place during the implantation process. Bacteria residing within said capsule can later move to the peritoneal cavity thereby causing peritonitis.

After implantation of a dialysis port in a patient, infection can arise from skin bacteria being transported through the skin by needle penetration through the skin and into the port. Bacteria, having entered the space between the external surface of the device and the opposed tissue surface, can then attach to the port outer surface and grow into colonies in a layer or film form called biofilm. While initially localized within the pocket formed around a device, such a colony may not cause symptoms or manifest as an infection for a long time. However, bacteria from the biofilm colony may shed and cross the pocket membrane, whereby an infection will manifest itself systemically and/or within the peritoneum. Such an infection can become a local tissue infection indicated by local swelling, formation of pus, local inflammation and pain, and so on, and it can also lead to systemic blood infection. Such infections are serious, and if not treated often lead to morbidity and even death.

Notwithstanding improvements in the construction of subcutaneous ports, infection problems still impede their full usefulness in medical practice. Such infections are difficult to treat, often requiring the removal of the port or other implanted device, thereby subjecting the patient to additional trauma and leaving the patient without benefit of the device for the time it takes to clear the infection and replace the removed implant with another device. Moreover, the need to administer antibiotics frequently is expensive, and patients who suffer from repeated infections often breed strains of bacteria resistant to antibiotics. Such infections create a dilemma for patients who will lose access to life-sustaining renal replacement therapy.

It is therefore an object of the current invention to provide a method for disinfecting and for providing infection prophylaxis with respect to dialysis solutions. It is a further object of this invention to provide means of disinfecting or providing infection prophylaxis of the interior of implanted devices and catheters used in association with peritoneal dialysis. It is yet a further objective of this invention to provide a system for the use of non-antibiotic antimicrobial substances which do not cause the development of drug resistant strains of bacteria within peritoneal dialysis solutions.

SUMMARY OF THE INVENTION

Figure 1:
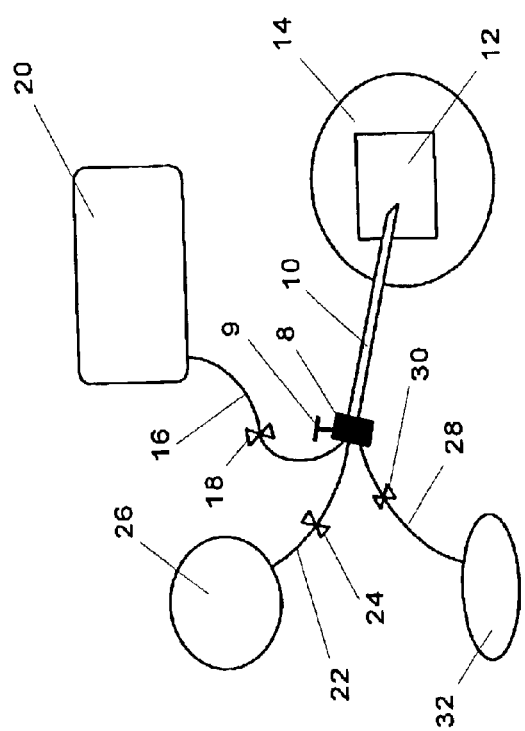
FIG. 1 depicts a typical hydraulic configuration for insertion of taurolidine solution into the dialysate catheter.

The invention comprises a composition and method for prevention and treatment of microbial infection in peritoneal dialysis comprising a liquid aqueous solution containing about 0.2% to about 4% taurolidine. The taurolidine is intended to prevent or reduce the incidence of infection within the abdomen and/or in the vicinity of an implanted dialysis port. In one embodiment, the taurolidine solution is used to lock or flush the catheters and ancillary tubing for peritoneal dialysis. In another embodiment, taurolidine is added to the peritoneal dialysis solution itself.

DESCRIPTION OF THE PREFERRED EMBODIMENTS

The present invention contemplates the incorporation of the antimicrobial compound taurolidine and in some embodiments adjuvants to taurolidine into water-based catheter flushing solutions and into PD solutions themselves. The taurolidine is intended to prevent or reduce the incidence of infection within the abdomen and/or in the vicinity of the implanted dialysis port.

Taurolidine is a non-antibiotic antimicrobial (i.e., both bactericidal and fungicidal) with clot preventive attributes. It has been used medically in Europe since the 1970s as an antiseptic solution and in gel and powder form as an antimicrobial for refractory bone infections. Taurolidine acts in a manner different from that of antibiotics and has never induced bacterial resistance by its bactericidal effects. More specifically, taurolidine reacts with the lipopolysaccharides of bacterial cell walls and with the polypeptides of bacterial endotoxins and exotoxins so as to kill bacteria and inactivate the toxins. Taurolidine is not an antibiotic in the usual sense, nor is it an antiseptic; the kill time of tauroldine in vitro ranges from 15 to 30 minutes while the definition of an antiseptic, according to the French standard (AFNOR), is less than 5 minutes. Taurolidine is therefore not an actual antiseptic but belongs rather within the group of local and systemically applied antimicrobial chemotherapeutic agents (Burri, C., p.2, "Local Treatment of Infections with Taurolin," in *Aktuel. Prob. Chir. Orthop.* 34:60–66, 1989.).

The chemical name for taurolidine is bis-(1,1-dioxoperhydro-1,2,4-thiabiazinyl-4) methane. The substance is a derivative of the aminosulfonic acid taurine (aka taurineamide).

The mode of antimicrobial activity of taurolidine is not precisely known but rather is the subject of informed conjecture. In simple aqueous solution, taurolidine exists in equilibrium with taurultam and methylol-donating species. Current consensus suggests hydrolysis of taurolidine in vivo to taurultam and methylol taurultam in equilibrium. Upon liberation of one active N-methylol (hydroxymethyl) group from methylol taurultam, taurultam is further hydrolyzed via methylol taurineamine to taurine. Thus three active N-methylol groups are liberated per molecule of taurolidine following reactions with bacterial or fungal cell constituents. These methylol groups have a high affinity for, and bind selectively and irreversibly to, bacterial cell wall constituents to exert their bactericidal effect. Because of this unique mechanism of action, there is no reason to suspect cross-resistance with standard antimicrobial agents that do not have this mechanism of action.

While the activity of taurolidine against bacterial species is modest by classical standards, taurolidine has a broad safety profile and can be given intravenously in high doses. The following factors are considerations in the present invention incorporating taurolidine into PD solutions:

Anti adherent

Bactericidal with respect to aerobic and anaerobic bacteria and fungi

Neutralizes endotoxins

Low cost

Does not induce resistant bacterial strains

Blenkham, J. I., "The Antimicrobial Activity of Taurolin: A Possible Additive for Parenteral Nutrition Solutions," *Clinical Nutrition* (1987) 6:35–38, briefly reviewed the antibacterial and related properties of Taurolin (taurolidine) and describes it as a unique substance for local, intraperitoneal and intravenous administration. Also, taurolidine has been successfully used as a peritoneal lavage in the past. Baker, D. M, Jones, J. A., Nguyen-Van-Tam, J. S., Lloyd, J. H., Morris, D. L., Bourke, J. B., Steele, R. J., and Hardcastle, J. D., A Taurolidine Peritoneal Lavage as Prophylaxis Against Infection After Elective Colorectal Surgery, *Br. J. Surg.* (1994) 81(7):1054–1056. It has an extraordinary broad antibacterial spectrum of action against gram-positive and gram-negative, aerobic and facultative and obligate anaerobic bacteria. It is also effective against most yeasts and filamentous fungi. Resistance has not been observed either in vivo or in vitro. The antimicrobial effect of taurolidine is also known to be lower in vitro than in vivo.

One of the most interesting properties of taurolidine is its ability to prevent adherence of bacteria to host cell surfaces and thus to block a key pathway in the pathogenesis of many infectious processes. Another important property of taurolidine is its considerable antiendotoxic activity both in vivo and in vitro. Thus taurolidine has a confirmed role in the prophylaxis of infection and in the treatment of extremely ill patients with life-threatening sepsis and endotoxic shock. Taurolidine is transported from the peritoneum to the blood by lymphatic absorption of peritoneal fluid at a rate of 0.5 to 1.5 ml/minute.

Lactate, Bicarbonate and Acid/Base Balance

The bicarbonate content of PD solutions does not necessarily correspond to that of plasma. In the body, blood sodium bicarbonate works as a buffer, maintaining the blood pH at a desired level of about 7.4. Because of problems involved in preparing and storing bicarbonate-containing dialysis solutions such as formation of insoluble precipitates, dialysis solutions normally contain lactate as a bicarbonate-generating compound. The typical PD-solution lactate level is 35 to 40 mEq/liter. Metabolism of the absorbed lactate in the liver and other organs results in the generation of bicarbonate. Normally only L-lactate is present in the body. However, the lactate used in peritoneal dialysis is racemic DL-form, as both isomers can work to generate bicarbonate. Citric acid, lactic acid or any other biologically acceptable acid can be used to lower the pH of the taurolidine solution, thereby increasing the solubility and effectiveness of taurolidine while also providing anticoagulant activity. An effective pH for the taurolidine solution is about 4 to about 7, with a preferred range of about 5.5 to 6.5.

Concentration of Taurolidine

The present invention contemplates the addition of between about 0.2% and about 4% by weight taurolidine into PD solutions. Concentrations lower than about 0.2% are not effective; and concentrations higher than about 4% may cause pain. Concentrations of about 0.2% to about 2% are preferred. The taurolidine is intended to prevent or reduce the incidence of infection within the abdomen and/or in the vicinity of an implanted dialysis port. Compounds such as citrate and polyvinyl pyrrolidione (PVP) can be used to prevent the formation of insoluble particles in concentrations of taurolidine exceeding about 2%.

One method by which to make use of the antimicrobial properties of taurolidine in connection with peritoneal dialysis is to dissolve it in the PD solution itself. Taurolidine is non-toxic to the patient even in very large amounts and has been used in Europe as a peritoneal lavage for some years. Related to this method is the invention of a peritoneal dialysis solution that contains taurolidine in a concentration of between about 0.5% and about 2%, with the additional constituent of a biologically acceptable acid such as those selected from the group comprising citrate and lactate.

FIG. 1 shows, in schematic format, a typical arrangement of fluid lines and dialysis solution reservoirs used in a peritoneal dialysis setup. FIG. 1 is used here to supplement the following descriptions of the several methods contemplated for making use of the antimicrobial properties of taurolidine and solutions of taurolidine in the prevention of infection and/or sepsis. More specifically, FIG. 1 shows a fluid bag or reservoir 20 holding a solution of taurolidine. The bag 20 is connected by way of a fluid conveying line 16, having a flow control valve 18, to a junction body 8 which communicates with a catheter 10 which, in turn, communicates with a port 12 disposed upon or close to that part of a patient's abdomen 14 adjacent the patient's abdominal cavity. (NOTE: The call-out number 14 is intended equally to denote the surface of the abdomen as well as the underlying abdominal or the peritoneal cavity.) The junction body 8 also receives a feed line 22, having a valve 24, which communicates with a reservoir 26 that holds fresh peritoneal dialysis solution. A third fluid line 28, having valve 30, communicates between the junction body 8 and a reservoir 32 that holds spent or used dialysis solution. Additionally, the junction body 8 has a catheter cutoff valve 9 that can control the flow of fluids into and out of the catheter 10 and peritoneal cavity 14. The valves 18 and 24 may include check valves to prevent unintended back flow of fluids into the respective reservoirs 20, 26.

The peritoneal dialysis setup illustrated schematically in FIG. 1 is for purposes of illustration only and is not intended to represent a specific arrangement, i.e., alternative arrangement having similar operational objectives are conceivable. For example, in the first method described below for using taurolidine as an antimicrobial in peritoneal dialysis, the reservoir 20 and the attendant line 16 and valve 18 are not contemplated.

In the following listing of methods by which to use taurolidine within a setup of the sort shown in FIG. 1, the concentration of taurolidine in solution is in the range of about 0.2% to about 2%. The pH is in the range of about 4 to about 7, preferably about 5.5 to 6.5. The pH is adjusted by the addition of biologically acceptable acids selected from the group comprised of lactic acid and citric acid.

The first method for conveying taurolidine solution into the catheter 10 is by passing a prescribed amount of the peritoneal dialysis solution from the fresh dialysis bag 26 through a cartridge (not shown) that is either in series with the line 22 or in parallel with the line 22, along with appropriate flow control valves, said cartridge containing taurolidine powder. The dialysis solution with dissolved taurolidine is then conveyed to the catheter 10, where it is allowed to reside for a period of time. That time may range from at least 1 minute before to the entire time period between flows in the catheter.

Another method of the present invention is to first fill the catheter 10 or the port 12 with a taurolidine solution of the above describe concentration for at least 1 minute before refilling the catheter or port with the peritoneal dialysis fluid.

Another method comprises, first, adjusting the appropriate valves to allow all the spent peritoneal dialysis fluid from the peritoneal cavity 14 to flow into the receiving reservoir 32, followed by adjustment of the respective valves 18, 24 and 30 so as to allow fresh dialysis solution from the reservoir 26 to flush both the fresh dialysis line 22 and the drain line or spent dialysate line 28. Next, valve 18 is opened while valve 24 and catheter cutoff valve 9 are closed, allowing taurolidine solution from reservoir 20 to flush the drain line 28. Then the valve 18 is closed and valve 24 is opened, thereby allowing fresh dialysis solution from reservoir 26 to flush the drain line 28. Valve 30 is then closed while catheter cutoff valve 9 and valve 18 are opened to allow a prescribed amount of taurolidine solution from reservoir 20 to fill the catheter 10, where the solution is held for at least 1 minute before being drained into the spent reservoir 32. Finally, valve 18 is closed and valve 24 is opened to allow fresh dialysis solution to flow into the peritoneal cavity 14.

A further method for flushing with taurolidine solution is to flush the catheter 10 after filling the peritoneal cavity 14 with fresh dialysis solution. This method comprises, first, filling the peritoneal cavity with fresh peritoneal dialysis fluid and then closing the valve 24. Next, the valves are adjusted so that so that fresh dialysis solution will flow into the spent reservoir 32, thereby flushing the line. Then the valve 18 is opened, allowing taurolidine solution to flush both the fresh dialysis line 16 and the drain line 28. Finally, the catheter 10 is filled with a prescribed amount of taurolidine solution.

I claim:

1. A method of inhibiting or reducing infection sepsis within the abdomen and/or in and around an implanted peritoneal dialysis access catheter either after infusion of fresh peritoneal dialysis fluid or between infusions, method comprising the steps of:
   (i) removing substantially all existing peritoneal dialysis fluid from the lumen of the access catheter;
   (ii) replacing the removed peritoneal dialysis fluid in the lumen of the access catheter with a solution comprising taurolidine in a concentration of between about 0.2% to about 4% by weight and additionally comprising citric acid in a sufficient amount to bring the pH of the solution into a range from about 4 to about 7; and
   (iii) leaving the solution comprising taurolidine in the lumen of the access catheter for a specified time period.

2. The method of claim 1 wherein the pH is brought to about 5.5.

3. The method of claim 1 where the specified time period is the time remaining until the next removal of spent peritoneal dialysis fluid.

4. The method of claim 1 where the specified time period is at least one minute.

5. A method of inhibiting or reducing infection sepsis within the abdomen and/or in and around an implanted peritoneal dialysis port either after infusion of fresh peritoneal dialysis fluid or between infusions, said method comprising the steps of:
   (i) removing substantially all existing peritoneal dialysis fluid from the lumen of the port;
   (ii) replacing the removed peritoneal dialysis fluid in the lumen of the port with a solution comprising taurolidine in a concentration of between about 0.2% to about 4% by weight and additionally comprising citric acid in a sufficient amount to bring the pH of the solution into a range from about 4 to about 7; and
   (iii) leaving the solution comprising taurolidine in the lumen of the port for a specified time period.

6. The method of claim 5 wherein the pH is brought to about 5.5.

* * * * *